United States Patent [19]

Schwarting et al.

[11] Patent Number: 5,096,810
[45] Date of Patent: Mar. 17, 1992

[54] MONOCLONAL ANTIBODIES FOR DIAGNOSIS OF HAIRY CELL LEUKEMIA

[75] Inventors: Roland Schwarting; Robert Evans, both of New York, N.Y.

[73] Assignee: Sloan-Kettering Institute For Cancer Research, New York, N.Y.

[21] Appl. No.: 838,588

[22] Filed: Mar. 11, 1986

Related U.S. Application Data

[63] Continuation of Ser. No. 546,858, Oct. 31, 1983, abandoned.

[51] Int. Cl.$^5$ .............. G01N 33/574; G01N 33/53; C07K 15/28; C12N 5/12
[52] U.S. Cl. .............. 435/7.23; 435/240.27; 435/172.2; 436/548; 436/813; 530/387; 530/808; 530/809; 935/103; 935/110
[58] Field of Search .............. 435/7, 68, 172.2, 948, 435/240.27; 436/548, 813; 935/103, 110; 530/387, 808, 809

[56] References Cited

U.S. PATENT DOCUMENTS 4,513,088 4/1985 Levy et al. .............. 435/7

OTHER PUBLICATIONS

Lanier et al., Eur. J. Immunol.; 15:713–718 (1985).
Schwarting et al., Blood, 65(4):974–983 (1985).
Posnett et al., J. Clin. Invest., 70:254–261 (Aug. 1980).
Springer et al., Eur. J. Immunol., 9:301–306 (1979).
Nadler et al., J. Immunol., 126(5):1941–1947 (1981).
Stashenko et al., J. Immunol., 125(4):1678–1685 (1980).
Abramson et al., J. Immunol. 126(1):83–87 (1981).
Nadler et al., J. Immunol., 131(1):244–250 (Jul. 1983).
Brooks et al., J. Immunol., 126(4):1373–1377 (1981).
Falini et al., Am. J. Clin. Path., 83:289–300 (1985).

*Primary Examiner*—Esther M. Kepplinger
*Assistant Examiner*—Susan L. Futrovsky
*Attorney, Agent, or Firm*—John P. White

[57] ABSTRACT

Monoclonal antibodies are described which are potent reagents for the immunologic definition of hairy leukemic cells.

S-HCL 1 is a pan-B cell marker with markedly increased staining on hairy cells versus normal B-lymphocytes. It also stains with a variety of B-cell leukemias and lymphomas, but is not crossreactive with any other cell type in man. With these features, it is also a useful reagent for the detection of human B-lymphocytes.

S-HCL-3 monoclonal antibody recognizes an antigen present on entirely different cell lineages, namely macrophages of almost all tissues and polymorphonuclear cells. This antigen is not expressed on any other malignant lymphocytes except hairy cells. Moreover, this antigen is not found on other non-Hodgkin lymphomas which may resemble hairy cell leukemia. Accordingly, b-HCl-3 is useful in the diagnosis of hairy cell leukemic.

6 Claims, No Drawings

MONOCLONAL ANTIBODIES FOR DIAGNOSIS OF HAIRY CELL LEUKEMIA

This present invention was wholly or partially made with funds provided by the Department of Human Health and Services under Grant No. CA 23766. Accordingly, the United States Government has certain rights in this invention.

This application is a continuation of U.S. Ser. No. 546,858, filed Oct. 31, 1983, now abandoned.

This invention concerns monoclonal antibodies which may be used to diagnosis hairy cell leukemia.

BACKGROUND

Since hairy cell leukemia was first described in 1958 (Bouroncle, B. A., Wiseman, B. K., Doan, C. A. Blood 13, 609 (1958)) the nature and cellular origin of this malignancy have been controversial. Originally termed "leukemic reticuloendotheliosis" due to the major involvement of the RES, it has become known under the more popular designation "hairy cell leukemia" by Schreck and Donnelly in 1966 (Schreck, R., Donnelly, W. J., Blood 27: 199, (1966)).

The diagnosis hairy cell leukemia is presently based on the electron and light microscopy appearance (Wright stain, supravital stain, phase contrast, slide chamber) of the leukemic cell. Typical ribosome-lamellar complexes in ultrastructural investigation have been observed prevalently in hairy cells but are also known in other malignancies (Daniel, M. T., Flandrin, G., Lab. Invest. 30: 1, (1974); Katayama, I., Li, C. Y., Yam, L. T. Am. J. Pathol. 69: 471, 1972; Katayama, I. Schneider, G. B. Am. JU. Pathol. 86: 163, (1977)). Furthermore, the diagnosis is supported by the evidence of tartrate resistent acid phosphatase (TRAP) first discovered by Yam et al. (Yam, L. T., Li, C. Y., Lam, K. W. N. Engl. J. Med. 284: 357, (1971). However, the latter phenomenon is indicative but not specific for hairy cell leukemia, and some hairy cells do not express this cytochemical marker (Katayami, I. Yang, J. P. S. Am. J. Pathol. 68: 268, (1977)). The resemblance to B-lymphocytes is obvious. Surface immunoglobulin is present with one or more heavy chain and monoclonal light chain expression. Presence of HLA DR antigen (Jansen, J., Turcker, W. L. B., Kersey, J. H. Blood 59: 609, (1982)), and absence of C3 receptor (Burns, G. F., Cawley, J. C., Barker, C. R., Hayhoe, F. G. J. Clin. Exp. Immunol. 29: 442, (1977)) are also characteristic findings in the majority of hairy cells.

Phagocytosis of latex particules and bacteria has been frequenctly described in in vitro studies of hairy cells (Polliack A. Braylan, R., Golomb, H. Lancet 2: 1013, (1974); Daniel, M. T., Supra (1974)). However, based on more recent reports, it is controversial whether a real internalization of those particles takes place or whether they get trapped within the extracellular space between the pseudopods (Jansen, J., Meijer, C. J. L. M., van der Valk, P., de Bruyn, W. C., Leijh, P. C. J., den Ottolander, G. J., van Further, R. Scand. J. Haematol. 23: 69, (1979)).

Accordingly, more specific, sensitive and reliable diagnostic tests for hairy ell leukemia have been sought.

SUMMARY

To illustrate the cellular origin, to provide helpful diagnostic reagents for the recognition of hairy cell leukemia, and to scribe hairy cell leukemia to a certain maturation stage within the B-cell lineage, a series of monoclonal antibodies against spleen cells obtained from a patient with this disease have been developed.

It has been discovered that monoclonal antibodies S-HCL 1 and 3 are potent reagents for the immunlogic definition of hairy leukemic cells.

S-HCL 1 is a pan-B cell marker with markedly increased staining on hairy cells versus normal B-lymphocytes. It also stains with a variety of B-cell leukemias and lymphomas, but is not crossreactive with any other cell type in man. With these features, it is also a useful reagent for the detection of human B-lymphocytes.

S-HCL-3 monoclonal antibody recognizes an antigen present on entirely different cell lineages, namely macrophages of almost all tissues and polymorphonuclear cells. This antigen is not expressed on any other malignant lymphocytes except hairy cells. Moreover, this atnigen is not found on other non-Hodgkin lymphomas which may resemble hairy cell leukemia (Neiman, R. S., Sullivan, A. R., Jaffe, R. Cancer 43: 329 (1979)), and other Sig+ malignancies which makes it a useful marker for distinguishing these malignancies for hairy all leukemia.

DETAILS

Availability of Monoclonal Antibodies

The hybridoma cell lines disclosed in the present invention bear the designated deposit number and are deposited with Sloan-Kettering Institute, 1275 York Avenue, New York, N.Y. 10021. Preferred hybridoma cell lines of the present invention are also deposited at the American Type Culture Collection, Bethesda, Md. and bear the following deposit numers:

| Monoclonal antibody # | ATCC # |
| --- | --- |
| S-HCL-1 | |
| S-HCL-3 | |

Deposit is for the purpose of enabling disclosure only and is not intended to limit the concept of the present invention to the particular materials deposited.

Preparation and Characterization of Monoclonal Antibodies

Cells Used for Immunization

Spleen cells from a patient with the diagnosis of hairy cell leukemia were cryopreserved in liquid nitrogen and thawed for both immunization and screening.

Spleen cells from a patient who presented the typical features of a hairy cell leukemia were used for immunization of mice. Surface marker studies of the leukemic cells demonstrated their resemblance to cells to the B-cell lineage (table 1). These hairy cells expressed surface immunoglobulins of the type o heavy and light chain. The majority of the cells was positive for the HLA DR antigen. The number of T-lymphocytes as determined with the Leu 1 and 4 antibody and by SRBC rosettes was low in this leukemic spleen.

Light and electron microscopy analysis exposed cells with the typical irregularities of the cell membrane. TRAP (tartrate resistent acid phosphatase) positivity of the leukemic cells also supported the diagnosis of hairy cell leukemia. The cells were also treated for a number of cell surface markers (SIg, HLA DR and rosette formation).

TABLE 1

Characterization of the immunizing hairy cells obtained from a patient who underwent splenectomy

| Surface markers | Percentage of positive cells |
| --- | --- |
| Heavy chains | 0 |
|  | 34 |
|  | 0 |
|  | 2 |
| polyvalent | 76 |
| light chains | 2 |
|  | 65 |
| Ia | 93 |
| Leu 1 | 7 |
| Leu 4 | 8 |
| Rosettes |  |
| EAC | 3 |
| SRBC | 10 |
| MRBC | 5 |
| tartrate resistant acid phosphatase | positive for the leukemic cells |
| morphology | typical "hairy" looking cells |

Immunization Protocol

Mice of an outbred strain (CD-1) were immunized i.p. with $10 \times 10^6$ hairy ells every ten days for a period of six weeks. The first immunization was applied i.p. in complete Freund's adjuvant (GIBCO, Wisconsin, U.S.A.). The last boost, three days before the fusion, was given as a membrane preparation of the leukemic cells. The cells were disrupted through repeated freezing and thawing procedure, the cell membrane proteins obtained by sequential centrifugation by methods known in the art (Stein, H., Gerdes, J., Schwab, U., Lemke, H., Mason, D. Y., Ziegler, A., Schienle, W., Diehl, V.: Identification of Hodgkin and Sternberg-Reed cells as a unique cell type derived from a newly detected small cell population. Int. J. Cancer: 30, 445 (1982)).

Fusion and Culturing of Cells

Fusion of murine splenocytes to the murine cell ilne WS-1 was carried out following the procedure of Oi and Herzenberg (Oi, V. T., Herzenberg, L. A.: Immunoglobulin-producing hybrid cell lines, in: Mishell: B. B., Shiigi, S. M.: Selected methods in cellular immunology, W. H. Freeman and Company, San Francisco, (1980)) with some variations. Briefly, $150 \times 10^6$ murine spleen cells were fused to the murine myeloma cell line in a ratio 5:1 using PEG 1000 (Fisher Scientific Co., Pennsylvania, U.S.A.) in a concentration of 50% (v/v) in RPMI 1640. Subsequently, the cells were plated out in flat bottom 96-well microculture plates (Linbro FB96TC, COnnecticut, U.S.A.) in RPMI 1640 containing 10% FCS (M. A. Bioproducts, Maryland, U.S.A.), 1% (v/v) P+S (GIBCO), 1% (v/v) glutamin (GIBCO), 0.1 mM hypoxanthine, 0.8M aminopterine, and 16M thyminidine. The cell concentration amounted to 200,000 per well, additionally, each well was supplemented with 15,000 murine peritoneal macrophages.

Initial Screen and Selection for Cloning

Supernatants from growing hybrids were tested by indirect fluorescence staining; reactivity with the immunizing hairy cells and peripheral mononuclear blood cells (PMBC) was evaluated using the fluorescence activated cell sorter (FACS IV, Becton & Dickinson, California, U.S.A.). Hybrids which produced immunoglobulin with most specificity for the immunizing cells were selected for coning by limiting dilution in flat bottom 96-well plates (Linbro) in hypoxanthine thymidine (HT) medium.

Large Scale Production of Monoclonal Antiboy

Mu/Nu mice from an outbred strain (CD-1) were injected i.p. with $50 \times 10^6$ immunoglobulin producing hybrid cells. Ascites and Sera of these mice were harvested after 10 to 20 days.

Indirect Fluorescence Staining

Blood cells from various sources including leukemic cell lines were tested for reactivity with the monoclonal antibodies S-HCL ⅓ by indirect fluorescence staining. Briefly, $10^6$ cells were incubated with 100 l of monoclonal antibody at a saturated concentration at 4° C. for 1 hour. The cells were washed twice in HBSS, and subsequently incubated with the second FITC (fluorescein isothiocyanate) labeled reagent for another hour at 4° C. Goat- -mouse FAB-fragments (Cappel, Pennsylvania, U.S.A.) were used as the second antibody. Positive staining was evaluated by FACS IV analysis. 1:50 diluted mouse serum and immunoglobulin bearing supernatants from irrelevant clones served as negative controls.

The specificity of these antibodies by fluocytometric analysis of a variety of normal cells from peripheral blood, tonsilla, spleen, and bone marrow showed that within the range of mononuclear cells, S-HCL 1 antigen was found to be present on all B-cells, whereas S-HCL 3 antigen was detected on monocytes or macrophages (table 2). In addition, S-HCL 3 was reactive with a smaller subpopulation of lymphoid cells in the peripheral blood.

Seven hairy cell specimen from patients that underwent splenectomy were tested for reactivity with the antibodies S-HCL 1 and 3 by FACS IV analysis, (Table 3). Without exception, all hairy cells exhibited bright staining with the monoclonal antibodies S-HCL 1 and 3. In particular, the staining of S-HCL 1 with hairy cells was much brighter than the staining with normal peripheral B-lymphocytes.

TABLE 2

Reactivity of the monoclonal antibodies S-HCL 1 and 3 with normal cells from peripheral blood, tonsilla, spleen, and bone marrow

|  | S-HCL 1 | S-HCL 3 |
| --- | --- | --- |
| peripheral blood cells |  |  |
| B-lymphocytes | + | ? |
| T-lymphocytes | − | − |
| monocytes | − | + |
| granulocytes | − | + |
| platelets | − | − |
| tonsillar cells |  |  |
| B-lymphocytes | + | − |
| T-lymphocytes | − | − |
| macrophages | − | + |
| spleen cells |  |  |
| B-lymphocytes | + | − |
| T-lymphocytes | − | − |
| macrophages | − | + |
| bone marrow cells | − | (+) subpopulation |

TABLE 3

Surface markers of seven hairy cell specimen tested by FACS IV analysis. All specimen are derived from spleen

| case No | S-HCL 1 | S-HCL 3 | Leu 1 | Leu 4 | Leu 5 | Ia | FAB polyvalent | FAB Ig A | FAB Ig M | FAB Ig D | FAB Ig G | Kappa | Lambda |
|---|---|---|---|---|---|---|---|---|---|---|---|---|---|
| 1 | +++ | +++ | − | − | − | + | +++ | (+) | − | (+) | +++ | − | ++ |
| 2 | ++ | ++ | (+) | − | − | ++ | ++ | + | − | − | ++ | − | ++ |
| 3 | +++ | ++ | (+) | (+) | (+) | + | +++ | − | − | ++ | ++ | +++ | − |
| 4 | +++ | +++ | − | − | − | + | +++ | + | − | − | +++ | − | +++ |
| 5 | ++ | ++ | − | (+) | − | ++ | ++ | ++ | − | − | − | − | ++ |
| 6 | +++ | +++ | (+) | − | − | +++ | +++ | − | − | ++ | − | − | +++ |
| 7 | ++ | ++ | (+) | − | − | ++ | + | + | − | + | − | − | ++ |

Indirect Immunoperoxidase Staining

Indirect immunoperoxidase staining of a variety of tissues and cytospin preparations was carried out by methods known in the art (Stein, H. Supra (1982). Briefly, lyophilized 8 m frozen tissue sections were fixed in acetone for 10 minutes, and subsequently fixed in chloroform for another 10 minutes, both at room temperature. The fixed sections were incubated with monoclonal antibody at saturated concentrations at room temperature. The monoclonal antibody was removed from the slides by washing in PBS, and then incubated with peroxidase conjugated rabbit- -mouse Ig (Dako, Copenhagen, Denmark) for 30 minutes, followed by a short wash. Prior to incubation, the antibody was absorbed to insolubilized human Ig, and then supplemented with human serum at a final concentration of 20% (v/v). In order to enhance the sensitivity of this method, a second peroxidse conjugated goat- -rabbit lg antibody (Medac, Hamburg, W. -German), absorbed and supplemented with human Ig as described above, was applied. Finally, the section were stained with diaminobezidine (0.6 mg/ml) and hydrogen peroxide (0.01%) for 10 minutes at room temperature. The sections were then washed in PBS and counterstained with Haemalum. S-HCL 1 was demonstrated by the staining method to be a pan-B lymphocyte antibody, and reacted with these cells in any lymphatic tissue. No cross-reactivity of this antibody with any other cell type was detected. Beside its reactivity with hairy cells, the reagent S-HCL 3 provied to be a useful marker for macrophages in almost all tissues. Table 4

TABLE 4

Staining of the monoclonal antibodies S-HCL 1 and 3 with a variety of tissues. All staining was carried out with the indirect immunoperoxidase technique

| Tissue, cells | S-HCL 1 | S-HCL 3 |
|---|---|---|
| lymphnode and tonsilla | | |
| macrophages | − | + (all) |
| stany sky macrophages | − | + |
| macrophages of the pulp | − | + |
| sinus histiocytes | − | + |
| fibrocytes/fibroblast | − | −/+ |
| follicular dentritic reticulum cells | − | − |
| interdigitating reticulum cells | − | − |
| thymus | | |
| macrophages (scattered in the cortex and medulla) | − | + |
| thymic nurse cells | − | − |
| medullary epithelial cells | − | − |
| medullary reticulum cells | − | − |
| thymocytes | − | − |
| B cells (few scattered in the medulla) | − | − |
| skin | | |
| epidermal cells | − | − |

TABLE 4-continued

Staining of the monoclonal antibodies S-HCL 1 and 3 with a variety of tissues. All staining was carried out with the indirect immunoperoxidase technique

| Tissue, cells | S-HCL 1 | S-HCL 3 |
|---|---|---|
| Langerhans cells | − | − |
| liver | | |
| hepatocytes | − | − |
| v. Kupffer cells | − | − |
| bile duct cells | − | − |
| kidney | | |
| glomerular cells | − | − |
| tubular cells | − | − |
| elongated intertubular cells (macrophage derived) | − | + |
| lung | | |
| pneumocytes I + II | − | − |
| bronchial cells | − | − |
| alveolar macrophages | − | + |
| spleen | | |
| white pulp (see lymphnode and tonsilla) | | |
| red pulp | | |
| sinus lining cells | − | − |
| macrophages | | |
| peripheral blood | | |
| B-cells | + | −? |
| T-cells | − | − |
| monocytes | − | + |

*Dendritio reticulum* cells and Langerhans cells in the skin failed to stain with this antibody. Staining tissues/cells from patients with different malignancies disclosed the unique simultaneous presence of S-HCL ⅓ Ag on hairy cells. This coexistence makes it feasible to distinguish hairy cell leukemia from any other B-cell derived malignancy. A variety of Non-Hodgkin lymphomas termed in compliance with the Kiel-classification (Table 4) reacted with the antibody SHCL 1, but did not react with the S-HCL 3 reagent. However, S-HCL 3 was reactive with acute myeloid (monocytic) leukemias, whereas S-HCL 1 was not reactive with those malignancies.

Specificity of Monoclonal Antibodies S-HCL 1 and 3 Among Cell Lines

In the course of determining the specificity of these two antibodies, we tested a number of cloned cell lines for reactivity with the S-HCL 1 and 3 (Table 6). Neither of the antibodies reacted with cell lines of T-cell lineage. S-HCl 3 did not react with these cell lines. According to expectation, two hairy cell derived cell lines of both virus and non-virus transformed original presented the surface antigens defined by the monoclonal antibodies S-HCL ⅓. The two myeloid cell lines KG-1 and Hl 60 failed to stain with antibody S-HCL 3, although this antibody was reactive with mature granulocytes.

TABLE 5

Reactivity of the monoclonal antibodies αS-HCL 1 and 3 with immunoperoxidase stained malignant cells or tissues.

| diagnosis source | No of cases | reactivity of the tumor cells S-HCL 1 | S-HCL 3 |
|---|---|---|---|
| hairy cell leukemia | 5 | + | + |
| B-CLL | 5 | + | − |
| inmunocytoma | 2 | + | − |
| follicular (centroblastic-centrocytic lymphoma) | 4 | + | − |
| centrocytic lymphoma | 3 | + | − |
| centroblastic lymphoma | 3 | + | − |
| lymphoblastic lymphoma of Burkitt type | 3 | + | − |
| immunoblastic lymphoma of B-type | 3 | + | − |
| lymphoblastic lymphoma of T-type | 4 | − | − |
| lymphomas of peripheral T-cell type | 5 | − | − |
| acute myeloid leukemia | 5 | | + |
| acute monocytic leukemia | 3 | | + |
| acute lymphatic leukemia (Null) | | | |
| chronic myeloid leukemia | | | |
| breast cancer | 4 | − | − |
| Hodgkin's disease | 5 | − | − |
| Hodgkin, Sternberg r. cells | | | |

TABLE 6

Reactivity of the monoclonal antibodies αS-HCL 1 and 3 with leukemic cell lines

| cell line origin EBV | S-HCL 1 | S-HCL 3 |
|---|---|---|
| Molt 4 | − | − |
| HSB | − | − |
| CEM T | − | − |
| Jurkat | − | − |
| SKL-7 | + | − |
| LN-1 | + | − |
| CESS | − | − |
| ARH | + | − |
| 8866 | − | − |
| HSB | − | − |
| BM-NH | + | − |
| BALL-1 | + | − |
| 1788 | − | − |
| BJA-B | + | − |
| 8226 | − | − |
| U 937 | − | + |
| K 562 | − | − |
| DAUDI | + | − |
| KG-1 | − | − |
| HL 60 | − | − |
| Jok 1 | + | + |
| Jok 2 | + | + |

Determination of Antiboyd Subclass

A double immunodiffusion of ascites derived monoclonal antibody against subclass specific rabbit- -mouse Ig (Miles, Research products, Indiana, U.S.A.) was carried out on readily available gel plates (Hyland Diagnostics, Illinois, U.S.A.). Precipitation lines were evaluated after 36 Hr. for determination of heavy chain subclass and light chain specificity.

Both antibodies S-HCl 1 and 3 belong to the murine immunoglobulin subclass Ig2b kappa. The antigen detected by the pan-B cell antibody S-HCL 1 was not related to either surface Ig or HLA Dr antigens. SDS-paging under reduced conditions visualized a single protein component of a molecular weight of approximately 150 kd. Monoclonal antibody S-HCL 3 recognizes two protein moieties of approximately 90 kd for the minor and 150–160 kd for the major component both reduced and non-reduced conditions.

Cell Surface Iodination, Immunoprecipitation, SDS-Page

A modification of the method of Marchalonis et al (Marchalonis, J. J., Cone, R. E., Santer, V.: Enzymatic iodination. A probe for accessible surface proteins of normal and neoplastic lymphocytes: Biochm. J. 124: 921, (197)) was applied to iodinate cell surface proteins. Briefly, $60 \times 10^6$ hairy cells previously washed three times, were resuspended in 1 ml PBS. 200 g of lactoperoxidase (Sigma, Missouri, U.S.A.), 2 Ci $^{125}$I and $3 \times 10$ l of a 0.3% $H_2O_2$ PBS solution were added intermittently to the cell suspension. Radiolabeled cell proteins were subsequently extracted in 0.5% NP 40 lysis buffer, and acid insoluble radioactivity determined by TCA precipitation. Radiolabeled surface protein was immunoprecipitated by monoclonal antibodies bound to protein A coated CL4B beads (PHarmacia, Uppsala, Sweden). The bound $125^I$ labeled surface antigens were eluted by boiling the beads in 4 m urea and 2% SDS in 0.1M Tris-HCL (pH 8.0) buffer. The eluted proteins then were subjected to SDS-polyacrylamide gel electrophoresis in a 5–20% polyacrylamide gradient gel. The gels were dried on filter paper, and the radiolabeled proteins visualized by autoradiography.

What is claimed is:

1. Hybridoma cell line ATCC No. HB 8414.
2. Hybridoma cell line ATCC No. HB 8415.
3. Monoclonal anitbody produced by the cell line of claim 1.
4. Monoclonal antibody produced by the cell line of claim 2.
5. Method of diagnosing hairy cell leukemia in an individual comprising assaying a cell sample from said individual with at least one monoclonal antibody selected from the group consisting of monoclonal antibodies produced by hybridoma cell lines ATCC No. HB 8414 and ATCC No. HB 8415 under conditions favoring formation of complexes between said monoclonal antibody and hairy cell leukemia cells, and determining the presence of said complexes.
6. Method as in claim 5, wherein said method is used to distinguish hairy cell leukemia cells from other forms of malignant lymphoma.

* * * * *